United States Patent [19]

Palazzetti et al.

[11] Patent Number: 4,620,799

[45] Date of Patent: Nov. 4, 1986

[54] NON-DESTRUCTIVE QUALITY-TESTING OF A JOINT BETWEEN SHEETS MADE BY ELECTRIC SPOT WELDING

[75] Inventors: Mario Palazzetti, Avigliana; Stefano Re Fiorentin, Grugliasco; Giovanni Tufano, Rivoli, all of Italy

[73] Assignee: Fiat Auto S.p.A., Italy

[21] Appl. No.: 737,644

[22] Filed: May 24, 1985

[51] Int. Cl.[4] .................................. G01N 25/72
[52] U.S. Cl. ............................ 374/5; 364/469; 374/57
[58] Field of Search .............. 374/5, 6, 7, 57, 29, 374/42

[56] References Cited

U.S. PATENT DOCUMENTS

| | | | |
|---|---|---|---|
| 2,264,968 | 12/1941 | De Forest | 374/7 |
| 2,323,715 | 7/1943 | Kuehni | 374/7 X |
| 2,852,850 | 9/1958 | Martin | 374/7 X |
| 4,362,057 | 12/1982 | Gottlieb et al. | 374/4 |

FOREIGN PATENT DOCUMENTS 0060251  4/1982  Japan .................................. 374/6

Primary Examiner—Daniel M. Yasich
Attorney, Agent, or Firm—Sughrue, Mion, Zinn, Macpeak, and Seas

[57] ABSTRACT

A method is described for the non-destructive testing of a joint obtained by the electrical spot-welding of two sheets of substantially the same material joined together in a local zone with the formation of a weld core which has a thermal diffusivity substantially different from the thermal diffusivity of the material of the two sheets before welding, such a core being obtained only when the welding is of a good quality.

The testing is effected by a device the main characteristic of which is an electrode which delivers heat and a detector electrode located at two conveniently chosen points on one surface or opposite surfaces of the two welded sheets. The detector electrode is connected through an amplifier and an analog-digital converter to a computer which processes the signal to provide an indication of the weld quality on the basis of the measured value of the thermal diffusivity.

7 Claims, 4 Drawing Figures

NON-DESTRUCTIVE QUALITY-TESTING OF A JOINT BETWEEN SHEETS MADE BY ELECTRIC SPOT WELDING

BACKGROUND OF THE INVENTION

The present invention relates to a device for the non-destructive quality-testing of a joint obtained by electrical spot-welding of two sheets joined together in a local zone with the formation of a core.

More particularly the present invention relates to a device for the non-destructive testing of the thickness of the welding core.

At present, known devices for the non-destructive testing of weld quality are based on ultrasonic testing and generally comprise an ultrasound generator and a detector for detecting an ultrasonic return signal. In use, the ultrasound generator is placed near the test piece so that ultrasonic waves pass through the test piece, the returning signal arriving at the detector delayed in proportion to the thickness of material traversed by the signal.

In the specific case of weld testing, if a weld core has not been formed, the ultrasound will be reflected at the air gap between the two pieces. If, on the contrary, there is no air between the two pieces, the detector will receive a signal confirming the presence of a weld.

The above described known devices, even if widely used, are not, however, suitable for measuring weld core thickness. Such devices simply reveal whether or not there is a discontinuity between the test pieces, but do not indicate whether a weld core or a simple bond has been formed. Furthermore the use of these devices is difficult in a factory, since they are bulky and the information which they provide is not sufficiently clear. It is known that whenever radiant heat impinges on the surface of a metallic object the radiation is partly absorbed and partly reflected by the object. The absorbed radiation causes a gradual heating of the whole object, due to the thermal diffusivity of the material.

There are devices able to determine the thermal diffusivity in a homogeneous metallic piece, the measured thermal diffusivity being characteristic of the material, whose composition may be unknown.

SUMMARY OF THE INVENTION

The present invention utilizes the fact that the weld core between two electrically spot-welded sheets, being constituted by material which has melted and then solidified again, has a structure with substantially different physical characteristics from those of the initial material, and in particular the thermal diffusivity of the weld core differs from that of the initial material.

The altered structure of the weld core can also be detected by other parameters which can be tested only by destroying the welded piece.

Laboratory researches and tests have shown that it is possible to test a weld non-destructively by detecting the thermal diffusivity of the weld core and of the initial material.

The object of the present invention is to provide a process for the non-destructive testing of a joint obtained by electrical spot-welding of two metallic sheets in a local zone with the formation of a weld core, the weld core having a substantially different thermal diffusivity from that of the initial material, the process comprising the following steps:

instantaneous heating of a point located on the outer surface of one of the two welded sheets;

measuring the rise in temperature at a conveniently chosen point on the surface of one of the two welded sheets;

temporarily storing the measured temperatures;

permanently storing the diffusivity values of the material;

permanently storing the diffusivity value of the sheets;

processing of the temperature signal, and determining the core thickness.

This object is realized by a device for the non-destructive testing of a joint formed by electrical spot-welding of two metallic sheets and substantially of the same type, in a local zone with the formation of a weld core, the structure of said core having a substantially different thermal diffusivity from that of the initial material, said device comprising:

a source of heat and an electrode forming a thermocouple with the sheet, arranged to be placed at two conveniently chosen points on the surface of at least one of the welded sheets;

a feeder for said source of heat;

a detector connected to the electrode to receive thermal signals from the latter;

an amplifier connected to the detector;

an analog-digital connected to the amplifier output, and a computer connected to the analog-digital converter for processing the digital signal and computing the thickness of the weld core.

BRIEF DESCRIPTION OF THE DRAWINGS

The invention will be further described, by way of example, with reference to the accompanying drawings, in which.

DETAILED DESCRIPTION OF THE ILLUSTRATED EMBODIMENTS

Figure 1:
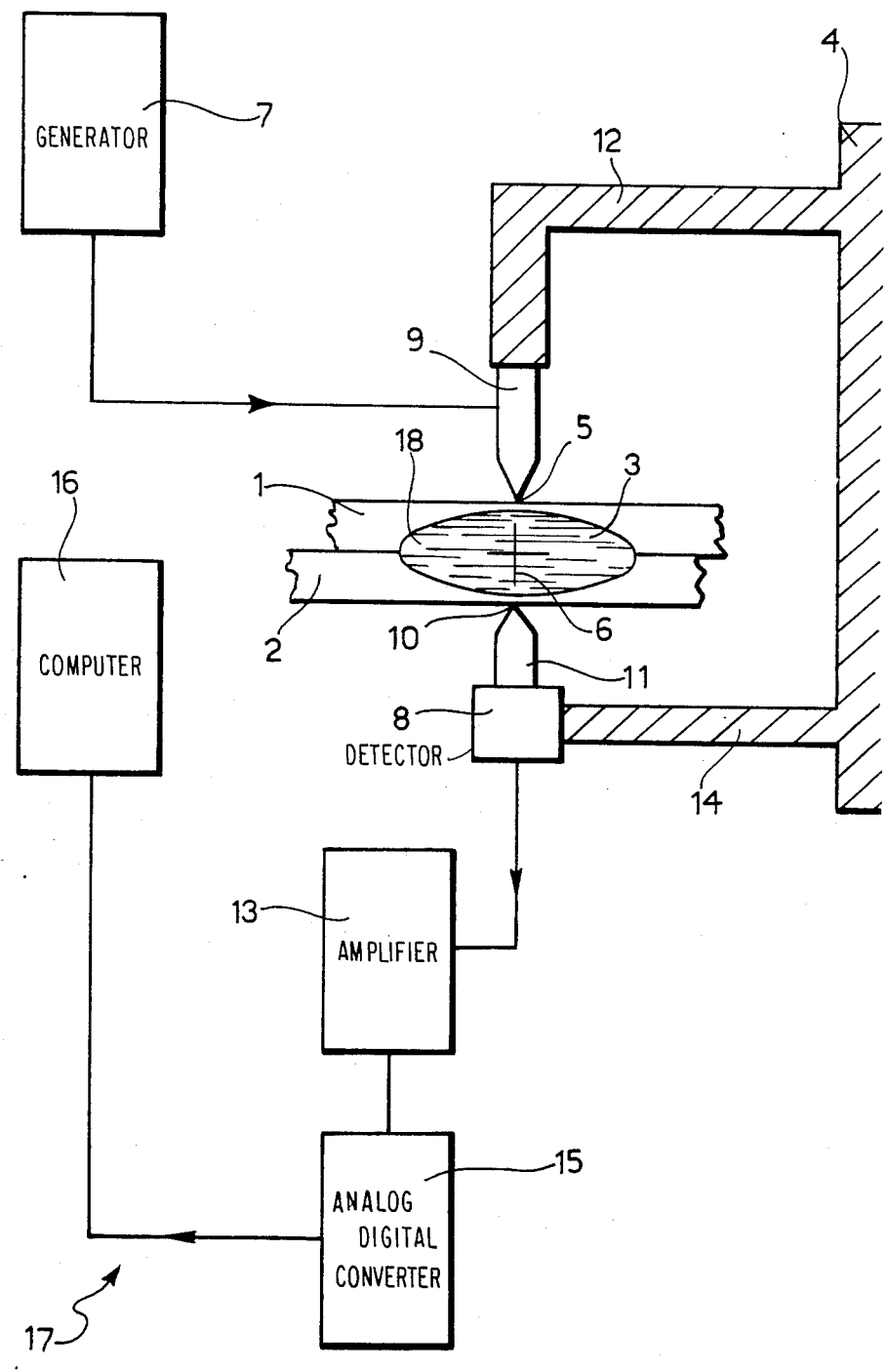
FIG. 1 shows schematically a device for testing weld quality, according to one embodiment of the present invention.

In the following description, referring to the accompanying drawings, the same reference numerals indicate the same elements.

Figure 2:
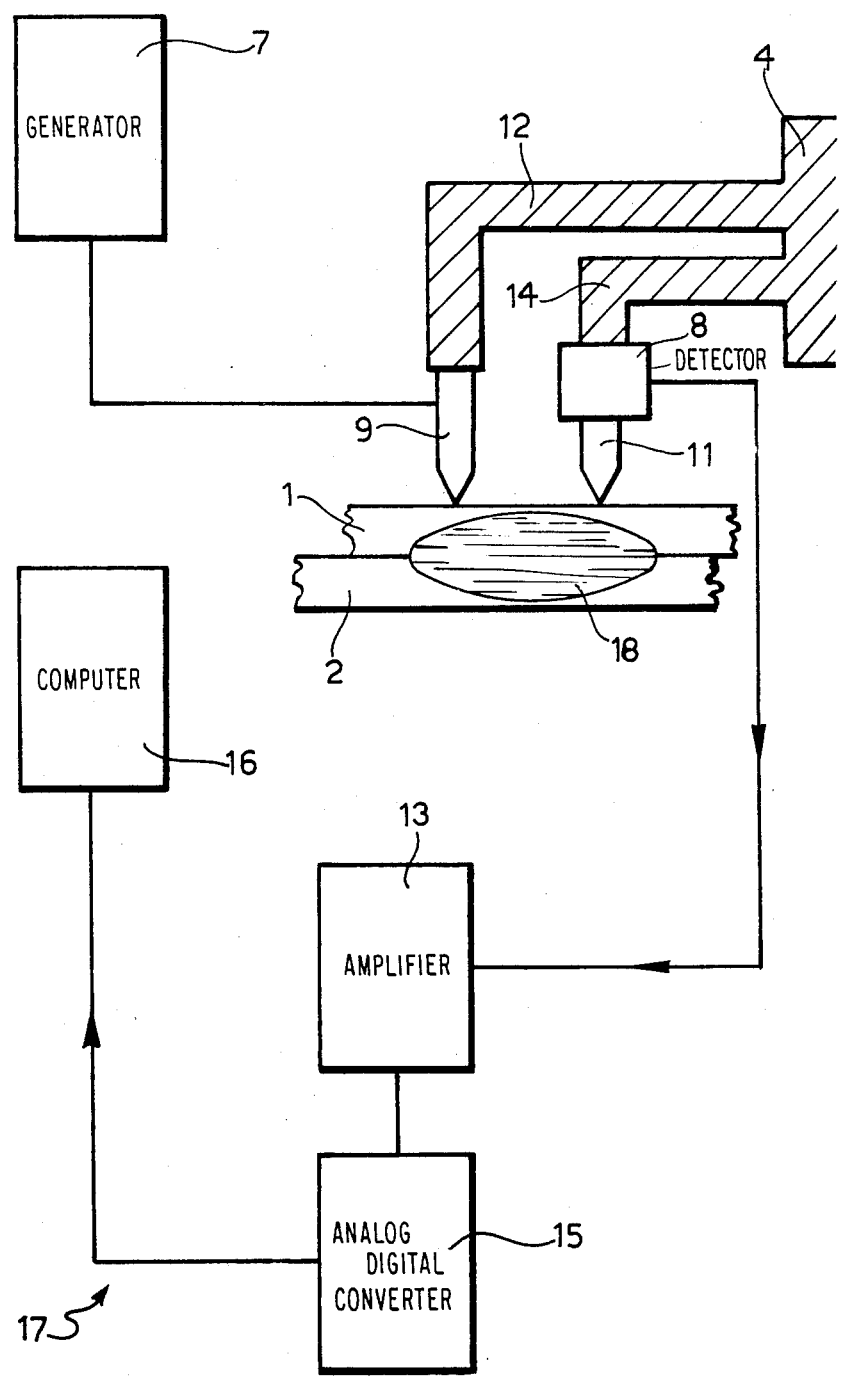
FIG. 2 shows a variant of the device shown in FIG. 1.

FIGS. 1 and 2 illustrate a device 17 for the non-destructive testing of an electrical spot-welded joint formed between two metallic pieces 1 and 2 in a local zone. When the welding is of good quality it results in the formation of a weld core 18, the structure of said weld core having a substantially different thermal diffusivity from that of the initial material or the material before welding.

The device 17 comprises an electrode 9 able to supply a predetermined quantity of heat in a very short time and a detector 8 connected to an electrode 11. The electrodes 9 and 11 are placed in contact with two conveniently chosen points 5 and 10 respectively on the surface of the two welded sheets 1 and 2.

In FIG. 1, the electrode 9 is positioned on point 5 on the sheet 1 coinciding with a line 6 perpendicular to the surface of the sheets 1 and 2, this line 6 passing through the centre 3 of the weld core 18. The electrode 11 is in contact with the point 10 on the sheet 2 directly opposite the point 5.

In FIG. 2, the electrodes 9 and 11 are positioned on the surface of only one of the two sheets 1.

Referring to FIGS. 1 and 2, a generator 7 feeds the electrode 9 and an amplifier 13 is connected to the detector 8. The output of the amplifier 13 is passed to an analog-digital converter 15.

The electrode 9 and the amplifier 13 are earthed by two cables, not shown.

The analog-digital converter 15 provides signals corresponding to the rise in temperature detected at the electrode 11, passing these signals to a computer 16 which processes said signals to provide an indication of the material diffusivity.

The electrode 9 and the detector 8 are supported, for example, by two arms 12 and 14 of a common support 4.

OPERATION

Figure 3:
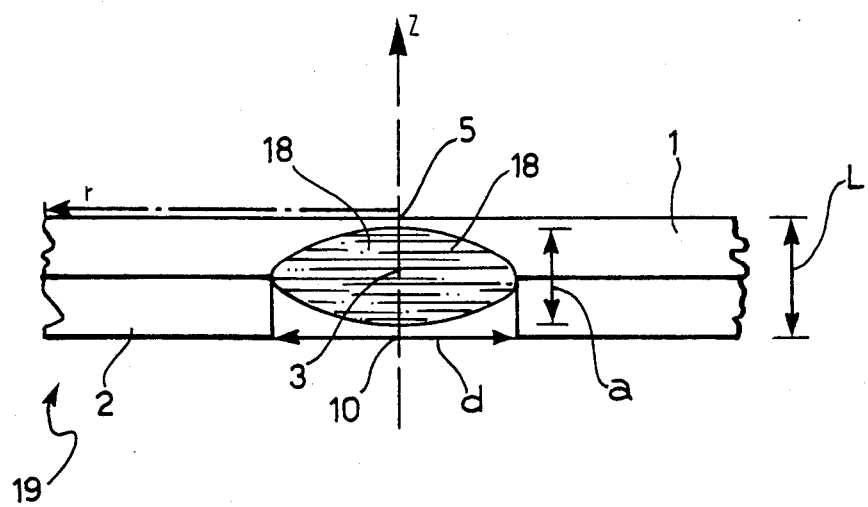
FIG. 3 shows diagrammatically the welding zone in FIGS. 1 and 2.
Figure 4:
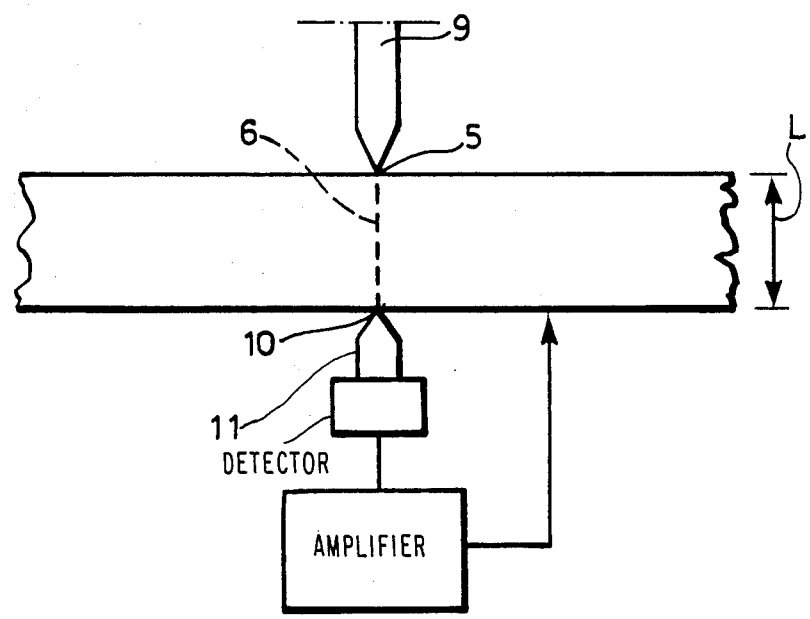
FIG. 4 shows schematically a device to measure the diffusivity of a test piece of homogeneous material.

The operation of the device 17 will first be considered from a theoretical standpoint, referring particularly to FIGS. 3 and 4.

With reference to FIG. 3, a test piece 19 is constituted by two sheets 1 and 2 joined together by melting a local zone to form a weld core 18 of thickness "a" and length "d". The core 18 is constituted by material in which a structure variation has taken place and heat transmission through this material occurs in a different way compared with that in the original material.

The distance between the two points 5 and 10 disposed on the line 6 perpendicular to the surface of the sheets 1 and 2 and passing through the centre 3 of the core 18 is indicated "L".

With reference to FIG. 4, the rise in temperature at the point 5 caused by the electrode 9 results in a temperature increase at the point 10, detected by the electrode 11.

The heat transmission between the points 5 and 10 of the test piece 19 is described by an equation giving the instantaneous temperature at any given point in terms of the thickness L of the sheet, the thermal diffusivity $a$ of the material; the heat input q at the point 5; the thermal conductivity K of the material; the temperature $T_O$ of the sheets 1 and 2 before the heating of the point 5 by the electrode 9 and the time t measured from the instant of the beginning of heating. The temperature T at a point defined by radial and axial coordinates r and z respectively from the point 5 (FIG. 3) at the time t is given by:

$$T(r,z,t) = T_O + \frac{q}{4\pi K L t} \cdot e^{\frac{-r^2}{4at}} \left[ 1 + 2 \sum_{n=1}^{\infty} \cos \frac{(n\pi z)}{L} \cdot e^{-n^2\pi^2 \frac{at}{L^2}} \right] \quad (A)$$

This equation can be used to derive the thermal diffusivity $a$, by comparing the graph of this function with the measured temperature values. If Cp is the specific heat, and if:

$$\theta = (T - T_O) \cdot \frac{\rho C p L^3}{q} \; ; \; \tau = \frac{at}{L^2} \; ; \; \zeta = \frac{z}{L} \; ; \; \rho = \frac{r}{L}$$

Then A becomes:

$$\theta(\rho,\zeta,\tau) = \frac{e^{-\frac{\rho^2}{4\tau}}}{4\pi\tau} \cdot \left[ 1 + 2 \sum_{n=1}^{\infty} \cos (n\pi\zeta) e^{-n^2\pi^2\tau} \right]$$

Comparing this function with the experimental data the ratio $a/L$ can be found, from which the diffusivity of the material can be deduced.

The variables $\rho$ and $\zeta$ are functions of the position of the electrode (11).

For example, when positioning the electrodes on opposite sides of the sheets, we have $\rho \approx 0$; $\zeta = 1$ $$\theta(0,1,\tau) = \frac{1}{4\pi\tau} \left[ 1 + 2 \sum_{n=1}^{\infty} (-1)^n e^{-n^2\pi^2\tau} \right]$$

On the contrary, when positioning the electrodes on the same side of the sheets, we have: $\rho \neq 0$; $\zeta = 0$ $$\theta(\rho,0,\tau) = \frac{e^{-\frac{\rho^2}{4\tau}}}{4\pi\tau} \left[ 1 + 2 \sum_{n=1}^{\infty} e^{-n^2\pi^2\tau} \right]$$

FIG. 4 illustrates the theoretical configuration adopted for measuring heat diffusivity on a laboratory test piece made of homogeneous material.

FIG. 1 shows a device for the non-destructive testing of the spot welding of two sheets 1 and 2 joined together by melting a local zone or a core 18 comprising a support structure 4 having an upper part 12 carrying a source of heat 9 fed by a generator 7.

This source 9 of a known type, can be constituted, according to requirements, by a xenon flash tube, by a solid state laser, by an electron beam or like heat generator, or by an electrical discharge between an electrode and the surface of the test piece, so to constitute a punctiform or point type heat source concentrated at a point 5 of the sheet 1 on the line 6 perpendicular to the surface of the sheets 1 and 2 and passing through the center of the core.

In this case it is better to use a source of heat (or of thermal energy) which is punctiform, that is, concentrated at a point, as heat supplied by other means affects a very wide surface and the measurement can be influenced by local variations of the absorption power of the surface and in order to avoid this inconvenience it would be necessary to screen the zone near the point 5 of the piece 1 with specific protective screening and the use of the above mentioned device would be less advantageous.

An electrode 11 is positioned at the point 10 on the surface of the sheet 2 directly opposite the point 5 of the electrode 9, the electrode 11 forming with the sheet 2, a thermocouple.

The electrode 11 can, for example, comprise a sintered alloy of constantan and tungsten carbide or constantan and aluminum having a ceramic part which acts as a rigid support, while the metal allows a high thermoelectric power.

This thermocouple formed between the sheet 2 and the electrode 11 is connected to a detector 8 fixed to the lower part 14 of the support structure 4. The detector 8 detects the rise in temperature caused by the heat transmitted form the electrode 9 through the two sheets 1 and 2 connected by the local weld.

The potential difference of the thermocouple is amplified by the amplifier 13 the output of which is converted by the analog-digital converter 15 interfaced with the computer 16, which stores the data as a comparative signal.

The computer 16, of a known type, is preferably a micro-processor and receives the signals from the analog-digital converter 15 duly processing them to derive the value of the coefficient of thermal diffusivity of the core 18. This value is compared with the value of the diffusivity of the initial material which is permanently stored in the computer 16, which is therefore able to derive from the signals the thickness of the core 18.

In the example illustrated in FIG. 2 the electrode 11 is placed on the piece 1 on the same side as that on which the electrode 9 is positioned. The electrode 9, the electrode 11, the detector 8, the amplifier 13, the analog-digital converter 15 and the computer 16 together constitute a device 17 for measuring the thickness of the core 18 of the weld between the two sheets 1 and 2.

The advantages of the embodiment illustrated in FIG. 2 are evident, since it is not in fact necessary to know the thickness of the two sheets joined together and it is possible in this way to provide an instrument of small size capable of effecting reliable quality testing of a spot-weld.

What is claimed is:

1. Device for the non-destructive testing of a joint between two metallic sheets of substantially the same material spot-welded together in a local zone with the formation of a weld core, the structure of said core having a substantially different thermal diffusivity from that of the initial material, said device comprising:
    a heat source means including a heat conveying path means for supplying heat to a first point on the surface of one of the sheets adjacent said core;
    an electrode adapted to form a thermocouple with the sheets at a second point on the surface of the sheets spaced from said first point to provide thermal signals;
    a detector connected to the electrode to receive thermal signals form the latter;
    an amplifier connected to the detector;
    an analog digital converter connected to the amplifier output; and
    a computer connected to the analog digital converter for processing the digital signal to determine the thickness of the weld core and the quality of the joint between the two sheets welded together.

2. The device defined in claim 1, wherein the heat source is punctiform.

3. The device defined in claim 1 wherein the electrode is constituted by a sintered alloy of constantan and tungsten carbide.

4. The device defined in claim 1, wherein the electrode is constituted by a sintered alloy of constantan and aluminum.

5. A process for the non-destructive testing of the joint between two sheets of metallic material spot welded together in a local zone with the formation of a weld core, the structure of said core having a substantially different thermal diffusivity from that of said material before welding wherein the process comprises:
    supplying a predetermined quantity of heat along heat conveying path means to a first point on the outer surface of one of the two welded sheets in proximity to said local zone;
    detecting the rise in temperature at another point on the outer surface of one of the two welded sheets in proximity to said local zone;
    generating a signal corresponding to the detected rise in temperature;
    processing said signal to compute the thermal diffusivity of said local zone wherein said weld core is formed; and
    comparing the thermal diffusivity of said local zone thus computed with the thermal diffusivity of said material before welding thereby deriving an indication of the thickness of said core and the quality of said joint between said two sheets welded together.

6. The process as set forth in claim 5 wherein the temperature rise is detected on the same surface of the sheets to which heat is applied.

7. The process as set forth in claim 5 wherein the heat is applied and the temperature rise is detected at directly opposite points on opposite surfaces of the two welded sheets.

* * * * *

UNITED STATES PATENT OFFICE
CERTIFICATE OF CORRECTION

Patent No. 4,620,799              Dated November 4, 1986

Inventor(s) Mario Palazzetti; Stefano Re Fiorentin; Giovanni Tufano

It is certified that error appears in the above-identified patent and that said Letters Patent are hereby corrected as shown below:

On the title page,
    [30]    Foreign Application Priority Data

May 24, 1984, Italy, 67526-A/84

Signed and Sealed this

Thirty-first Day of March, 1987

*Attest:*

DONALD J. QUIGG

*Attesting Officer*      *Commissioner of Patents and Trademarks*